US006736782B2

(12) United States Patent
Pfeiffer et al.

(10) Patent No.: US 6,736,782 B2
(45) Date of Patent: May 18, 2004

(54) APPARATUS, COMPUTER PROGRAM, CENTRAL VENOUS CATHETER ASSEMBLY AND METHOD FOR HEMODYNAMIC MONITORING (75) Inventors: Ulrich J. Pfeiffer, Munich (DE); Thorsten Burger, Munich (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 10/083,108

(22) Filed: Feb. 27, 2002

(65) Prior Publication Data

US 2002/0120204 A1 Aug. 29, 2002

(30) Foreign Application Priority Data

Mar. 1, 2001 (EP) .............................. 01104995

(51) Int. Cl.$^7$ .............................. A61B 5/02; A61B 5/00

(52) U.S. Cl. ...................... 600/481; 600/483; 600/549

(58) Field of Search ................................ 600/481, 483, 600/485, 486, 300, 549, 407; 607/96, 100, 113

(56) References Cited

U.S. PATENT DOCUMENTS

| | | | |
|---|---|---|---|
| 3,651,318 A | | 3/1972 | Czekajewski |
| 4,217,910 A | * | 8/1980 | Khalil ........................ 600/483 |
| 4,236,527 A | | 12/1980 | Newbower et al. |
| 4,507,974 A | | 4/1985 | Yelderman |
| 5,217,019 A | | 6/1993 | Hughes |
| 5,509,424 A | * | 4/1996 | Al-Ali ........................ 600/505 |
| 5,701,908 A | | 12/1997 | Carlson et al. |
| 5,857,976 A | * | 1/1999 | Quinn et al. ................ 600/506 |
| 5,954,659 A | * | 9/1999 | Curley et al. ............... 600/505 |
| 6,033,383 A | | 3/2000 | Ginsburg |

FOREIGN PATENT DOCUMENTS

| | | |
|---|---|---|
| DE | 198 14 371 A1 | 10/1999 |
| EP | 0 947 941 A2 | 10/1999 |
| FR | 2.112.767 | 6/1972 |

OTHER PUBLICATIONS

Dollar M L et al: "Evaluation of A Continuous Thermodilution Cardiac Output Catheter" Asaio Journal, US, J.B. Lippincott Co., Hagerstown, Md., vol. 38, No. 3, Jul. 1, 1992, pp. 351–356.
European Search Report.
Corresponding to U.S. Application Ser. No.: 09/282,421.

* cited by examiner

Primary Examiner—Max F. Hindenburg
Assistant Examiner—Navin Natnithithadha
(74) Attorney, Agent, or Firm—Nixon Peabody LLP; Donald R. Studebaker (57) ABSTRACT A central venous cather (1) is placed in the vena cava superior (2) and equipped with a heating coil (3) for emitting heat pulses in the immediate proximity of the distal end (5) of the catheter (1) in order to introduce travelling temperature deviations to the patient's circulation. The power transferred to the blood stream during emission of each heat pulse represents an input signal for modified thermodilution measurements. Each travelling temperature deviation is detected as a system response corresponding to an input signal, when it reaches an arterial catheter (14) which additionally comprises a pressure sensor (17) for measuring the local blood pressure in the arteria femoralis (16) as a function of time. The computer (18) has stored thereon an executable computer program for repeatedly determining a reference cardiac output value from a plurality of input signals and corresponding system responses by thermodilution curve evaluation methods and for determining from the blood pressure function hemodynamic parameters by pulse contour analysis methods using the most recent respective reference cardiac output value for quasi-continuous recalibration.

37 Claims, 6 Drawing Sheets

APPARATUS, COMPUTER PROGRAM, CENTRAL VENOUS CATHETER ASSEMBLY AND METHOD FOR HEMODYNAMIC MONITORING

BACKGROUND OF THE INVENTION

1. Field of the Invention

The present invention relates to an apparatus, a computer program, a central venous catheter assembly and a method for hemodynamic monitoring.

2. Description of the Related Art

One of the most relevant parameters in hemodynamic monitoring is cardiac output, which currently is usually measured using intermittent bolus thermodilution measurements as described e.g. in U.S. Pat. Nos. 3,651,318, 4,217,910 and 4,236,527.

For bolus thermodilution measurements a certain amount of a liquid at a temperature higher or lower than blood temperature is injected as a bolus through a catheter which is placed in the blood stream of a patient, and the temperature deviation of the blood as a function of time is monitored at a place downstream from the place where the bolus is injected. The Cardiac Output CO can then be determined by algorithms based on the Stewart-Hamilton-equation:

$$CO = \frac{V_L(T_B - T_L)K_1 K_2}{\int \Delta T_B(t) dt}$$

where $T_B$ is the initial blood temperature, $T_L$ is the bolus temperature, $V_L$ is the bolus volume, $K_1$ and $K_2$ are constants to consider the specific measurement setup, and $\Delta T_B(t)$ is the blood temperature deviation as a function of time with respect to the baseline blood temperature $T_B$.

According to the prior art, usually pulmonary artery catheters are used injecting the bolus through a lumen outlet substantially apart from the distal end of the catheter and detecting the temperature deviation of the blood as a function of time at the distal end of the catheter.

In a typical measurement procedure, a cold bolus of saline at ice or room temperature in an amount of about 5–10 milliliters, or as a guideline 0.1 ml/kg body weight is injected through the pulmonary catheter. Completion of this procedure takes about 2 minutes. In order to obtain sufficient accuracy, it is repeated several times and the results are averaged. Using this conventional method, determining one reliable cardiac ouput value thus requires a measurement time of up to 10 minutes and involves the injection of up to 50 ml of fluid into the cardiovascular system of the patient and, as a consequence, can be carried out only one or two times per hour.

Instead of using cold bolus injections, heating pulmonary artery catheters are used for modified thermodilution methods such as described in U.S. Pat. Nos. 4,507,974 and 5,217,019. Periodic heat pulses at a given pattern are introduced substantially apart from the distal end of the catheter by a heating coil or a thermal filament mounted to the indwelling catheter. Temperature changes of the blood heated passing the heating coil or thermal filament, respectively, are measured downstream by a thermistor at the distal end of the catheter. Cardiac output is determined quasi-continuously based on the data sampled for several minutes using signal processing and averaging algorithms. Thus, the cardiac output values determined are average values over periods of several minutes. Accuracy of modified thermodilution methods using heating pulmonary catheters is sensible to high and unstable blood temerature.

The amount of heat which can be introduced the way described above is limited to avoid a thermocoagulation of the blood or damage to the tissue adjacent to the heater. Approaches to regulate the heat transferred by the catheter are described in U.S. Pat. Nos. 5,701,908 and 5,857,976.

Generally, the use of pulmonary artery catheters is rather highly invasive and includes risks for the monitored patient, such as malignant arrythmias and pulmonary artery rupture or infarction. The so called transpulmonary thermodilution method is less invasive applying a central venous catheter instead of a pulmonary artery catheter. A thermal indicator is injected through a lumen of the central venous catheter and an additional arterial catheter, introduced for example into the femoral artery, is used to detect the thermodilution curve after the thermal indicator has passed the heart. Again, completion of this procedure takes several minutes and is not suitable for repeated cardiac output determinations within short time intervals.

Pulse contour analysis is a continuous method to determine cardiac output by multiplying the heart rate by a beat-to-beat stroke volume for each heart beat. The stroke volume is determined from the shape of and the area under the arterial blood pressure curve of the systole, wherein the arterial blood pressure is measured in the femoral artery or other large artery. In the currently commercially available System PiCCO by Pulsion Medical Systems AG, Germany the so called pulse contour cardiac output PCCO is determined using the relation $$PCCO \propto HR \int_{Systole} \left( \frac{p(t)}{SVR} + C(p) \cdot \frac{dp}{dt} \right) dt$$

wherein HR is the heart rate, p(t) the time dependent driving blood pressure (i.e. the time dependent arterial blood pressure AP(t) measured minus the mean central venous blood pressure CVP), dp/dt the first derivative of p(t) with respect to time, SVR the systemic vascular resistance and C(p) the aortic compliance function of the monitored patient. The integral is determined for the systolic phase. Calibration is achieved by conventional cold bolus injection transpulmonary thermodilution methods. The compliance function C(p) characterizes the volume change and subsequent pressure change of the aorta due to the ability of the aorta to expand during the systole and recontract during the diastole. C(p) and SVR also have to be determined by using a reference thermodilution measurement. A method and an apparatus to determine the compliance function C(p) are described in DE 19814371 A1 enclosed herewith by reference. In order to achieve reliable results over an extended period of time, recalibration is necessary. According to the current state of the art, in clinical practice the time consuming recalibration procedure of carrying out a conventional cold bolus injection transpulmonary thermodilution measurement is usually performed every 8 hours.

BRIEF SUMMARY OF THE INVENTION

It is therefore an objective of the present invention to provide means rendering possible continuous recalibration of pulse contour measurements with only short time intervals between two respective recalibration steps. It is also an objective of the present invention to increase accuracy in determining hemodynamic parameters and, at the same time, keep the invasiveness of applying the medical equipment necessary as low as possible.

In order to accomplish these objectives, the present invention provides an apparatus for hemodynamic monitoring, which comprises a central venous catheter assembly comprising at least one lumen and heating means in the immediate proximity of the distal end of the central venous catheter assembly. The heating means are adapted to emit heat pulses for introducing travelling temperature deviations to a patient's blood circulation. The apparatus further comprises means for determining the power transferred by the heating means as a function of time. The power transferred during emission of each heat pulse thereby represents an input signal corresponding to the respective heat pulse. The apparatus further comprises an arterial catheter assembly comprising temperature sensing means for measuring the local blood temperature in an artery of the patient as a function of time, thus determining for each input signal a corresponding system response. The apparatus further comprises computing means having implemented thereon executable operations for determining a reference cardiac output value of the patient from at least one input signal and respective corresponding system response.

In a preferred embodiment of the invention the computing means has additionally implemented thereon executable operations for determining global end-diastolic volume and/or intrathoric blood volume and/or extravascular thermovolume of the patient from at least one input signal and respective corresponding system response.

In another preferred embodiment of the invention the central venous catheter assembly is adapted to emit the heat pulses at random or at at least one predefined pattern, such as sinusoidal waves or step functions with predefined amplitudes and durations.

In another preferred embodiment of the invention the heating means comprise an electrically heatable filament or heating coil.

In another preferred embodiment of the invention the heating means are means for emitting electromagnetic radiation comprising a fiberoptic bundle which is either insertable into a lumen of the catheter assembly or mounted into a lumen of the catheter assembly.

In another preferred embodiment of the invention the electromagnetic radiation is modulated electromagnetic radiation at different wavelenghts.

In another preferred embodiment of the invention the fiberoptic bundle comprises at least one fiber adapted to collect reflected radiation at the different wavelengths and the computing means additionally has implemented instructions thereon to determine from the reflected radiation the central venous oxygen saturation.

In another preferred embodiment of the invention, the central venous catheter assembly comprises means, e.g. a pressure sensor mounted into one of the lumina of the central venous catheter assembly, for measuring the central venous blood pressure. Preferably, the means are adapted to measure the central venous blood pressure continuously or intermittently.

In another preferred embodiment of the invention determining the reference cardiac output value includes statistic evaluation of a plurality of the input signals and respective corresponding system responses.

In another preferred embodiment of the invention the arterial catheter assembly additionally comprises pressure sensing means for measuring the patient's arterial blood pressure AP(t) as a function of time, thus creating an arterial blood pressure curve, and the computing means has implemented thereon executable operations for repeatedly determining hemodynamic parameters from the arterial blood pressure curve by pulse contour analysis using the reference cardiac output value.

In another preferred embodiment of the invention the computing means additionally has implemented thereon instructions to recalculate the hemodynamic parameters obtained from the arterial blood pressure curve and the reference cardiac output value after determining the reference cardiac output value.

In another preferred embodiment of the invention, the central venous catheter assembly comprises an additional lumen for thermal indicator injection. Thus a cold bolus transpulmonary thermodilution measurement can be used to obtain an initial reference cardiac output value for initial calibration.

In order to accomplish the above mentioned object, the present invention also provides a computer program for hemodynamic monitoring, which comprises instructions executable by a computer system to repeatedly perform the steps of
  (a) determining a reference cardiac output value by statistic evaluation of a plurality of input signals and respective corresponding system responses, the input signals representing the power transferred during emission of a plurality of heat pulses as a function of time, the heat pulses introducing travelling temperature deviations to a patient's blood circulation, the corresponding system responses being determined by measuring the local blood temperature in an artery of the patient as a function of time, and
  (b) determining hemodynamic parameters from an arterial blood pressure curve by pulse contour analysis using the reference cardiac output value, the arterial blood pressure curve being determined by measuring the arterial blood pressure in an artery of the patient as a function of time.

In order to accomplish the above mentioned object, the present invention also provides a hemodynamic monitoring method comprising the steps of
  (a) providing a central venous catheter assembly having a proximal end and a distal end, the central venous catheter assembly comprising at least one lumen and heating means in the immediate proximity of the distal end,
  (b) emitting heat pulses through the heating means for introducing travelling temperature deviations to a patient's blood circulation,
  (c) determining the power transferred by the heating means as a function of time, the power transferred during emission of each heat pulse thereby representing an input signal corresponding to the respective heat pulse,
  (d) providing an arterial catheter assembly comprising temperature sensing means and pressure sensing means
  (e) measuring through the temperature sensing means the local blood temperature in an artery of the patient as a function of time, thus determining for each the input signals a corresponding system response,
  (f) measuring through the pressure sensing means the patient's arterial blood pressure AP(t) as a function of time, thus creating an arterial blood pressure curve, and
  (g) determining a reference cardiac output value of the patient from at least one the input signal and the respective corresponding system response.
Hemodynamic parameters are repeatedly determined from the arterial blood pressure curve by pulse contour analysis using the reference cardiac output value.

In a preferred embodiment of the invention determining the hemodynamic parameters comprises the steps of
(1) calculating a mean arterial blood pressure MAP from the measured arterial blood pressure AP(t),
(2) calculating a systemic vascular resistance SVR of the patient according to the formula $$SVR=(MAP-CVP)/CO_{ref}$$

wherein CVP is an arbitrary central venous pressure which is measured (preferably continuously or intermittently), ascertained or estimated, and $CO_{ref}$ is the reference cardiac output,
(3) calculating the driving blood pressure p(t) according to the formula $$p(t)=AP(t)-CVP$$

(4) calculating at least the first derivative of the driving blood pressure with respect to time $\dot{p}(t)=dp/dt$, and
(5) determining the hemodynamic parameters from at least p(t), $\dot{p}(t)$ and SVR according to a non-linear model.

In another preferred embodiment of the invention the step of determining the hemodynamic parameters from at least p(t), $\dot{p}(t)$ and SVR according to a non-linear model includes determining a blood flow q(t) on the basis of the driving blood pressure p(t) and the first derivative with respect to time $\dot{p}(t)$, and calculating a compliance function according to $$C(p) = \frac{q(t) - p(t)/SVR}{\dot{p}(t) - Z(p) \cdot (\dot{q}(t) - \dot{p}(t)/SVR)}$$

for arbitrary impedance functions Z(p) and arbitrary times t in such a way that $$q(t) = \frac{p(t)}{SVR} + C(p)\left[\dot{p}(t) - Z(p) \cdot \left(\dot{q}(t) - \frac{\dot{p}(t)}{SVR}\right)\right]$$

is optimally satisfied.

In another preferred embodiment of the invention the hemodynamic parameters comprise pulse contour cardiac output PCCO and/or stroke volume SV and/or stroke volume variation SVV.

In order to accomplish the above mentioned object, the present invention also provides a central venous catheter assembly for hemodynamic monitoring, which comprises at least one lumen and heating means in the immediate proximity of the distal end.

In a preferred embodiment of the invention the lumen into which a fiberoptic bundle for emitting electromagnetic radiation for introducing travelling temperature deviations to the patient's blood circulation is insertable or mounted has an opening closer to the distal end of the catheter assembly than all the openings of all the other lumina of the catheter assembly.

BRIEF DESCRIPTION OF THE DRAWINGS

The accompanying drawings, which are not true to scale in order to improve clarity, serve for a better understanding of the above and other features of the present invention and are briefly described hereinbelow.

FIG. 4a schematically illustrates a preferred embodiment of a central venous catheter assembly according to the present invention.

FIG. 4b shows an enlarged view of the distal end portion of the venous catheter assembly of FIG. 4a.

FIG. 4c schematically shows a cross-sectional view of the distal end portion of the catheter assembly of FIGS. 4a–b with plane of section Z–Z'.

FIG. 4d schematically shows a cross-sectional view of the elongated body of the catheter assembly of FIGS. 4a–c with plane of section Y–Y'.

DETAILED DESCRIPTION OF THE INVENTION

Figure 1:
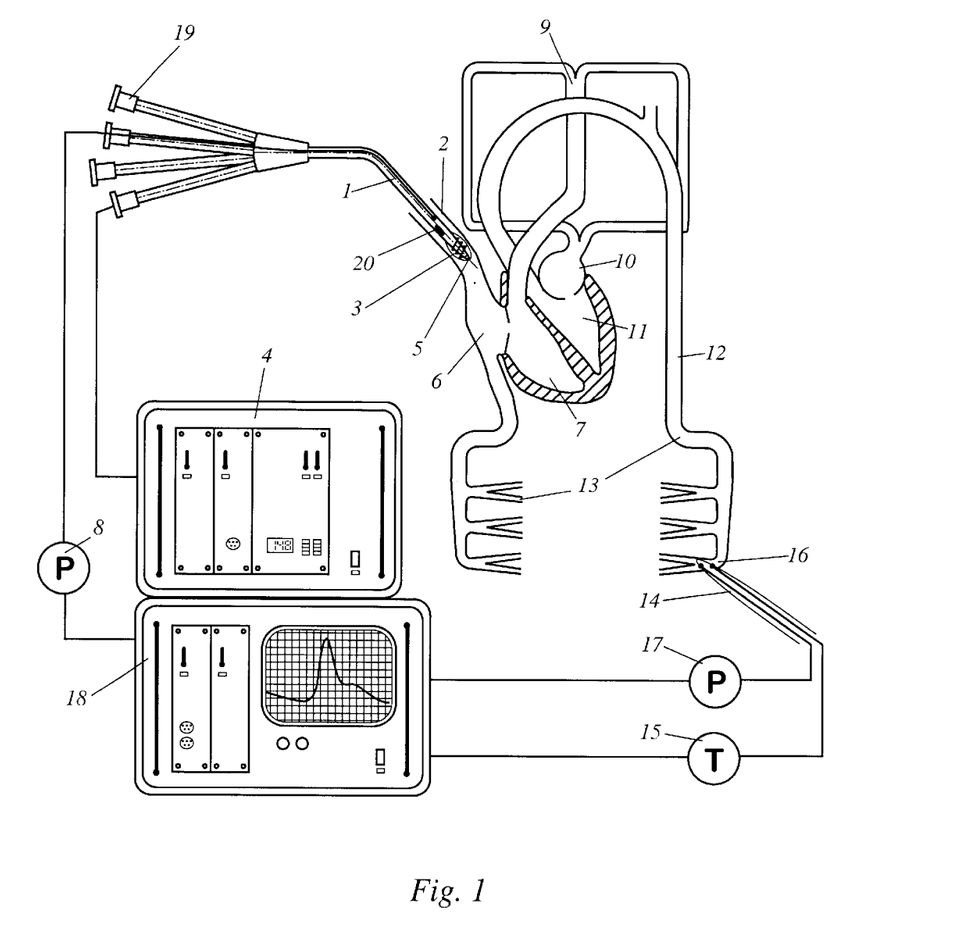
FIG. 1 schematically shows both a patient's heart and vascular system, which are subject to hemodynamic monitoring, and a preferred embodiment of an apparatus according to the present invention.

FIG. 1 schematically illustrates the main components necessary to implement an embodiment of an apparatus according to the invention. A central venous cather 1 is placed in the vena cava superior 2 of a patient. An electrically heated heating coil 3 is connected via one lumen of the catheter 1 with a current source 4 to emit heat pulses in the immediate proximity of the distal end 5 of the catheter 1 in order to introduce travelling temperature deviations to the patient's circulation. The current source includes circuitry to determine the power transferred to the patient's blood stream as a function of time. The power transferred to the blood stream during emission of each analysis methods, using the most recent respective reference cardiac output value to quasi-continuously recalibrate pulse contour analysis. From the same measurement, the global enddiastolic volume GEDV, the intrathoracic blood volume ITBV and the extravascular thermal volume ETV can also be obtained quasi-continuously.

Additionally, one lumen 20 of the catheter 1 can be used to inject a cold bolus through the corresponding proximal port 19 in order to perform a transpulmonary thermodilution measurement and to thus obtain an initial reference cardiac output value for fast initial calibration of the pulse contour analysis.

Figure 2:
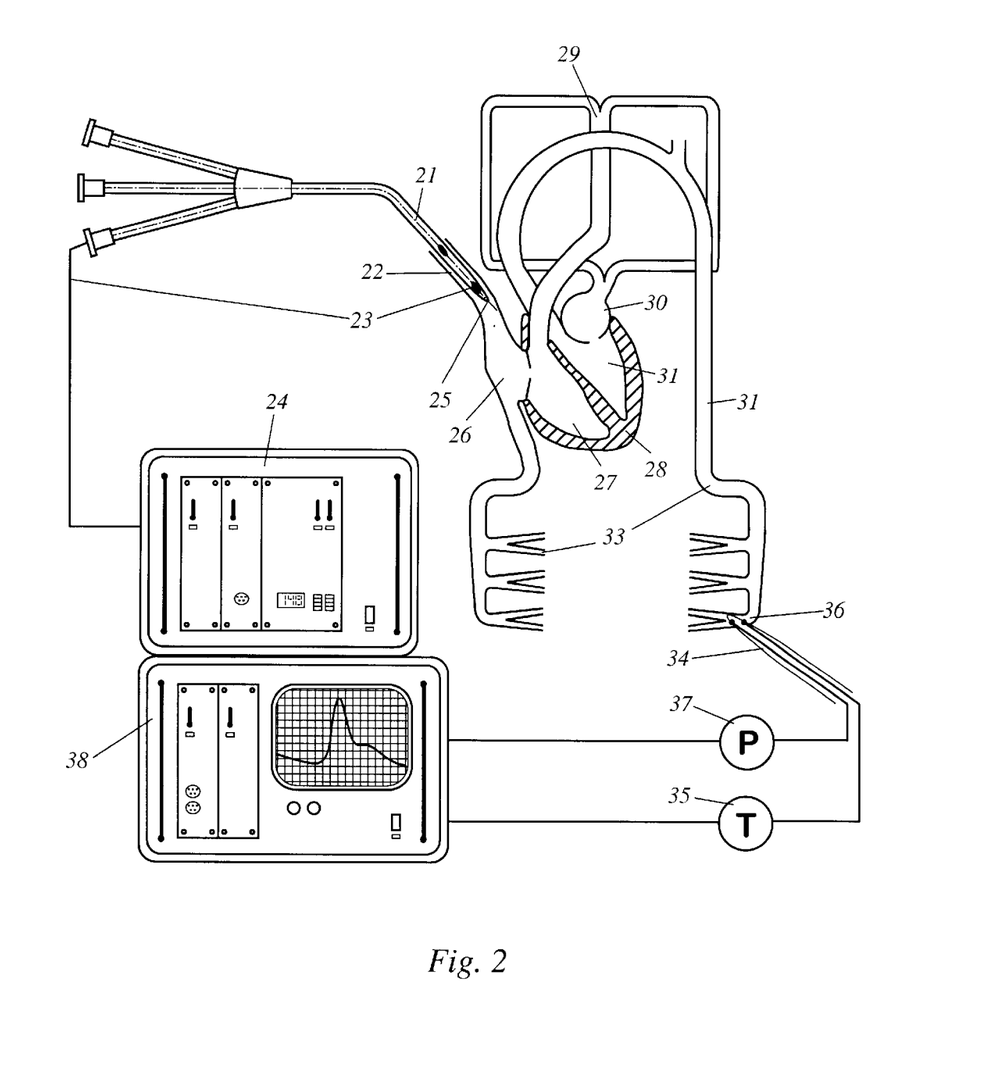
FIG. 2 schematically shows both a patient's heart and vascular system, which are subject to hemodynamic monitoring, and another preferred embodiment of an apparatus according to the present invention.

FIG. 2 schematically illustrates the main components necessary to implement another embodiment of an apparatus according to the invention. A central venous cather 21 is placed in the vena cava superior 22 of a patient. A fiberoptic bundle 23 is connected with a light source device 24 to conduct light pulses through the catheter 21 and thus emit heat pulses in the immediate proximity of the distal end 25 of the catheter 21 in order to introduce travelling temperature deviations to the patient's circulation. The light source device 24 is adapted to emit the light pulses at a predefined pattern and includes circuitry to determine the power transferred as a function of time. The power transferred during emission of each heat pulse represents an input signal for modified thermodilution measurements.

Additionally, a portion of the fibers of the fiberoptic bundle 23 can be used to transmit reflected light from the blood back to a detector (not shown) integrated into the light source device 24. If the light emission is modulated with different wavelengths, i.e. one wavelength that is substantially absorbed by the blood and one reference wavelength that is mostly reflected, the information of the reflected radiation can be used to control the energy, which is transferred to the patients blood stream. If, furthermore, the wavelengths are chosen to be within the range of wavelengths commonly used in spectrometric blood oxygen saturation measurements, the central venous blood oxygen saturation can be determined by the reflected intensities for the various wavelengths.

The travelling temperature deviations pass right atrium 26 and right ventricle 27 of the patient's heart 28, the pulmonary circulation 29 and left atrium 30 and left ventricle 31 of the patient's heart 28 to enter through the aorta 32 the systemic value for fast initial calibration of the pulse contour analysis.

FIG. 2 schematically illustrates the main components necessary to implement another embodiment of an apparatus according to the invention. A central venous cather 21 is placed in the vena cava superior 22 of a patient. A fiberoptic bundle 23 is connected with a light source device 24 to conduct light pulses through the catheter 21 and thus emit heat pulses in the immediate proximity of the distal end 25 of the catheter 21 in order to introduce travelling temperature deviations to the patient's circulation. The light source device 24 is adapted to emit the light pulses at a predefined pattern and includes circuitry to determine the power transferred as a function of time. The power transferred during emission of each heat pulse represents an input signal for modified thermodilution measurements.

Additionally, a portion of the fibers of the fiberoptic bundle 23 can be used to transmit reflected light from the blood back to a detector (not shown) integrated into the light source device 24. If the light emission is modulated with different wavelengths, i.e. one wavelength that is substantially absorbed by the blood and one reference wavelength that is mostly reflected, the information of the reflected radiation can be used to control the energy, which is transferred to the patients blood stream. If, furthermore, the wavelengths are chosen to be within the range of wavelengths commonly used in spectrometric blood oxygen saturation measurements, the central venous blood oxygen saturation can be determined by the reflected intensities for the various wavelengths.

The travelling temperature deviations pass right atrium 26 and right ventricle 27 of the patient's heart 28, the pulmonary circulation 29 and left atrium 30 and left ventricle 31 of the patient's heart 28 to enter through the aorta 32 the systemic circulation 33. An arterial catheter 34 is equipped with a temperature sensor 35 for measuring in an artery 36 of the patient, e.g. in the patient's arteria femoralis or axillary artery, the local blood temperature as a function of time. Thus each travelling temperature deviation is detected as a system response corresponding to an input signal for modified thermodilution measurements, when it reaches the arterial catheter 34. Additionally, the arterial catheter 34 comprises a pressure sensor 37 for measuring the local blood pressure in the artery 36 as a function of time.

The light source 24 as well as both the temperature sensor 35 and the pressure sensor 37 are connected to a computer 38 in order to transfer the input signals, respective system responses and arterial blood pressure readings to the memory of the computer 38, thus rendering the raw measurement data accessable for appropriate processing. The computer 38 has stored thereon an executable computer program comprising instructions to repeatedly determine a reference cardiac output value from a plurality of input signals and corresponding system responses by known thermodilution curve evaluation methods and to determine from the arterial blood pressure function hemodynamic parameters, such as pulse contour cardiac output PCCO, stroke volume SV and stroke volume variation SVV by pulse contour analysis methods, using the most recent respective reference cardiac output value to quasi-continuously recalibrate pulse contour analysis. From the same measurement, the global enddiastolic volume GEDV, the intrathoracic blood volume ITBV and the extravascular thermal volume ETV can also be obtained quasi-continuously.

Figure 3A:
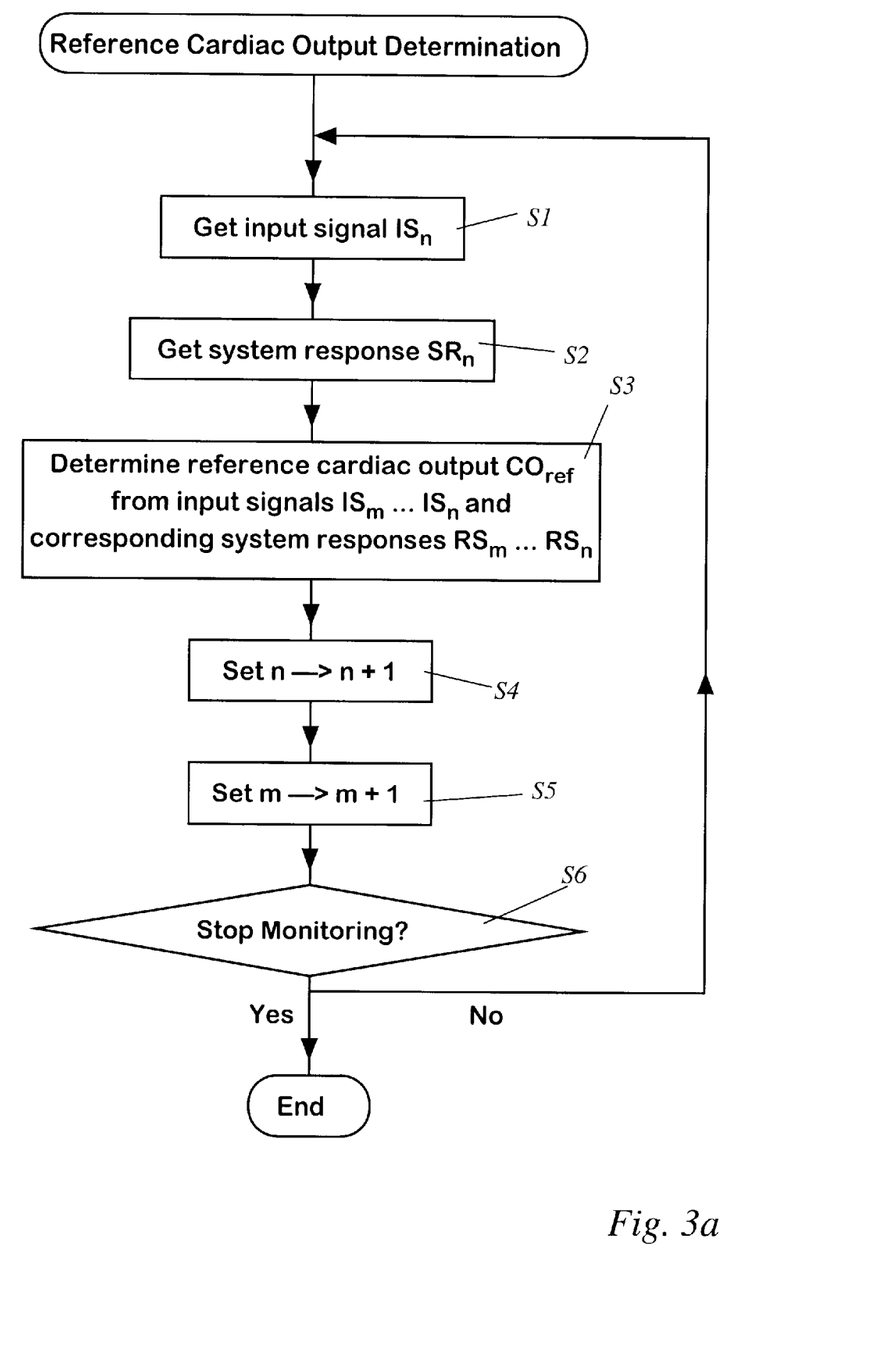
FIG. 3a is a flowchart illustrating the step sequence of the routine for reference cardiac output determination in an embodiment of a computer program according to the present invention performing the computation steps of a hemodynamic monitoring method according to the present invention.

FIG. 3a is a flowchart illustrating the step sequence of the routine for reference cardiac output determination in an embodiment of a computer program according to the present invention, presuming that the n-th system response corresponding to the n-th heat pulse emitted into a patient's blood stream has been detected. The n-th input signal $IS_n$ characterizing the n-th travelling temperature deviation introduced into the patient's blood stream and the n-th system response $SR_n$ characterizing the travelling temperature deviation detected downstream in patient's femoral artery, are acquired (Steps S1, S2). Reference cardiac output $CO_{ref}$ is determined by well-known Stewart-Hamilton method from a thermodilution curve extracted from the most recent n-m system responses $SR_m \ldots SR_n$ and the respective n-m input signals $IS_m \ldots IS_n$ applying appropriate averaging and signal processing algorithms (Step S3). Counter variables n and m are both raised by one (Steps S4, S5). If no stop command is entered, the routine will be carried out again beginning with step S1 (Step S6).

Figure 3B:
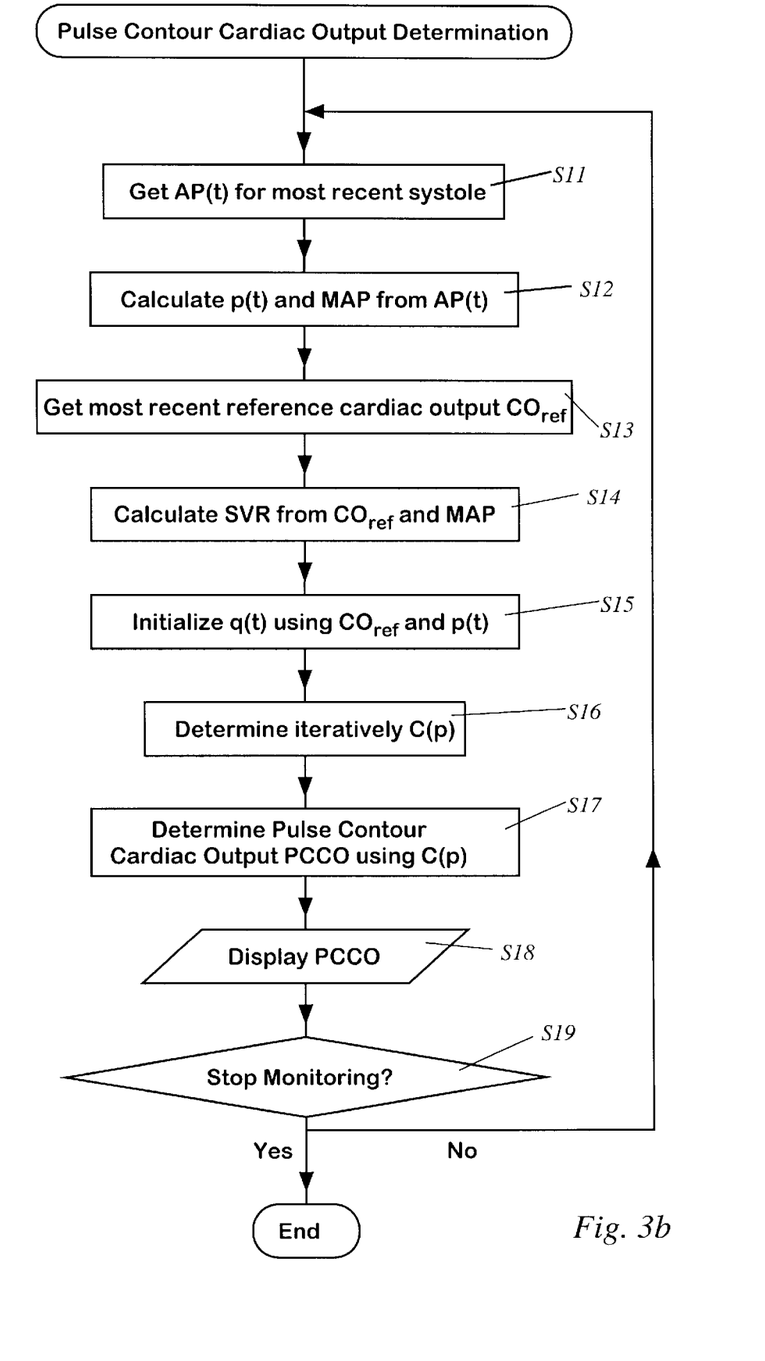
FIG. 3b is a flowchart illustrating the step sequence of the routine for pulse contour cardiac output determination in an embodiment of a computer program according to the present invention performing the computation steps of a hemodynamic monitoring method according to the present invention.

FIG. 3b is a flowchart illustrating the step sequence of the routine for pulse contour cardiac output determination in an embodiment of a computer program according to the present invention. The arterial blood pressure curve AP(t) of the most recent systole is acquired (Step S11). Then, the driving blood pressure p(t) and the mean arterial blood pressure MAP are calculated (Step S12). For calibration, the most recent reference cardiac output $CO_{ref}$ is acquired (Step S13) and used to calculate the systemic vascular resistance SVR (Step S14) according to the formula $$SVR=(MAP-CVP)/CO_{ref}$$

wherein CVP is a central venous pressure which is contiuously or intermittently measured. Blood flow value q(t) is initialized using $CO_{ref}$ and p(t) (Step S15). The compliance function C(p) is determined iteratively (Step S16) according to the formula $$C(p) = \frac{q(t) - p(t)/SVR}{\dot{p}(t) - Z(p) \cdot (\dot{q}(t) - \dot{p}(t)/SVR)}$$

for arbitrary impedance functions Z(p) and arbitrary times t, wherin ṗ(t) is the first derivative of p(t) with respect to (dp/dt), until the condition $$q(t) = \frac{p(t)}{SVR} + C(p)\left[\dot{p}(t) - Z(p) \cdot (\dot{q}(t) - \frac{\dot{p}(t)}{SVR}\right]$$

is optimally satisfied. Pulse contour cardiac output PCCO is calculated (Step S17) using the relation $$PCCO \propto HR \int_{Systole} \left(\frac{p(t)}{SVR} + C(p) \cdot \frac{dp}{dt}\right)dt$$

wherein HR is the heart rate. Then PCCO is displayed and may be stored in a file or printed (Step S18). If no stop command is entered, the routine will be carried out again beginning with step S11 (Step S19).

Figures 4A, 4B, 4C, 4D:
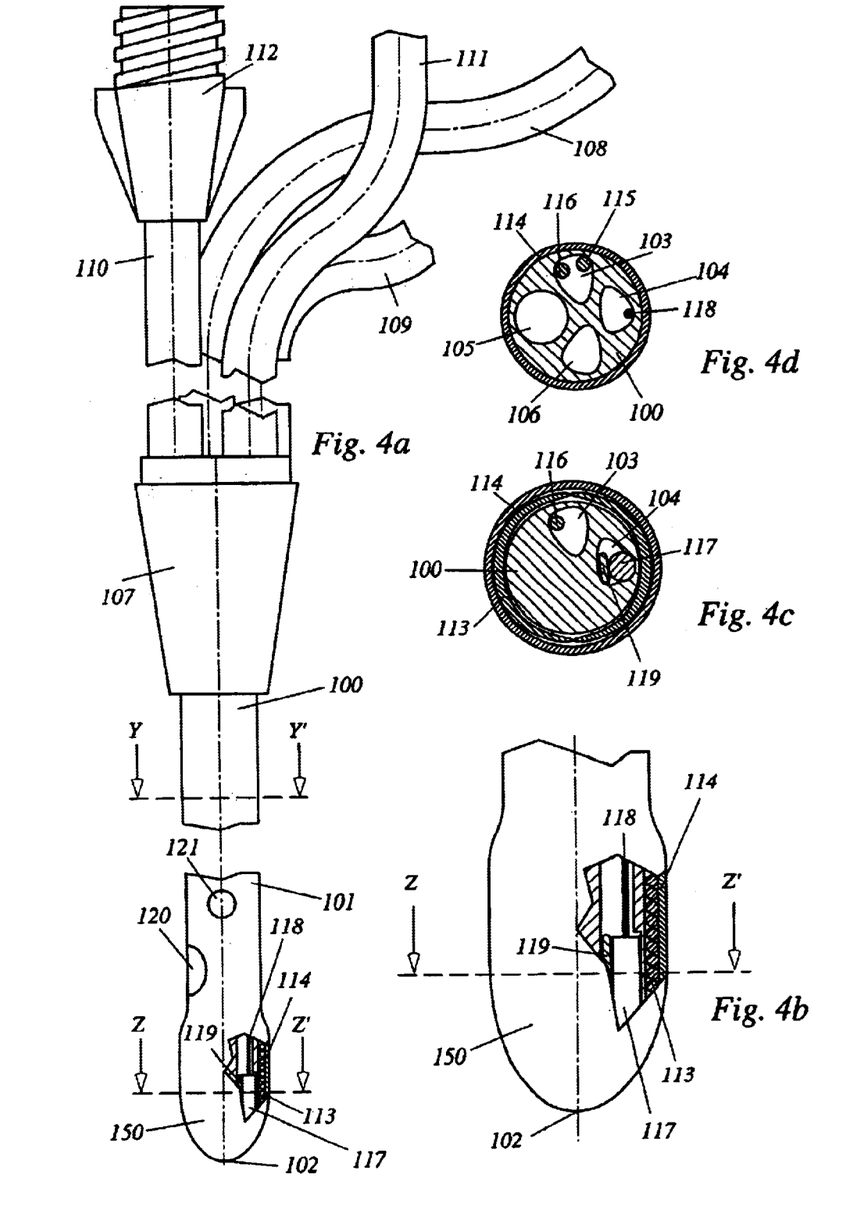

FIGS. 4a–d schematically illustrate a central venous catheter assembly embodying the present invention with FIG. 4b showing an enlarged view of the distal end portion 150 of the venous catheter assembly of FIG. 4a, FIG. 4c showing a cross-sectional view with plane of section indicated Z–Z' in FIGS. 4a–b and FIG. 4d showing another cross-sectional view with plane of section indicated Y–Y' in FIG. 4a. In both FIG. 4a and FIG. 4b the distal end portion 150 is shown partially in a longitudinal sectional view (indicated by hatchings) to schematically illustrate the interior of the distal end portion 150. The catheter assembly includes an elongated catheter body 100 including an intravascular catheter portion 101 adapted to be inserted, distal end 102 first, in a patient's vena cava superior. The catheter body 100 comprises a first lumen 103, a second lumen 104, a third lumen 105 and a fourth lumen 106. From a catheter body junction 107 located at the proximal end of the catheter body 100 the lumina 103, 104, 105, 106 further extend within respective separated channels 108, 109, 110, 111 to respective proximal ports (only one of which is shown as proximal port 112), through which the lumina 103, 104, 105, 106 are accessable. The intravascular catheter portion 101 has a length of approximately 15 cm and is capable of flexing during insertion but has sufficient rigidity to allow unproblematic handling and to prevent the lumina 103, 104, 105, 106 from collapsing. An electrically heatable heating coil 113 covered by a heat conducting surface layer 114 extends in several windings around the catheter body 100 close to the distal end 102. The heating coil is wired to an electrical power source (not shown) by connecting leads 115, 116 in the first lumen 103. The heating coil is adapted to emit heat pulses in the immediate proximity of the distal end 102, thus transmitting energy from the electrical power source to the patient's blood stream once the intravascular catheter portion 101 has been inserted into the vena cava superior. The thermal energy transferred to the blood by emitting each heat pulse represents a respective input signal for modified transpulmonary thermodilution measurements in the context of hemodynamic monitoring and can be determined by considering the temperature of the heating coil 113 measured by a temperature sensor 117 being in thermal contact with the heating coil 113 and placed into second lumen 104. The temperature sensor 117 is connected via cable 118 with suitable measurement data acquisition circuitry and firmly held in its position by a positioning member 119. The third lumen 105, which has an outlet 120 and can be accessed at proximal port 112, can be used to inject a thermal indicator for transpulmonary thermodilusion measurements (for calibration purposes) once the intravascular catheter portion 101 has been inserted into the vena cava superior. The fourth lumen 106 with outlet 121 can be used to apply a pressure sensor (not shown) to measure the central venous blood pressure. The catheter assembly may comprise additional lumina for other purposes.

Figures 5A, 5B:
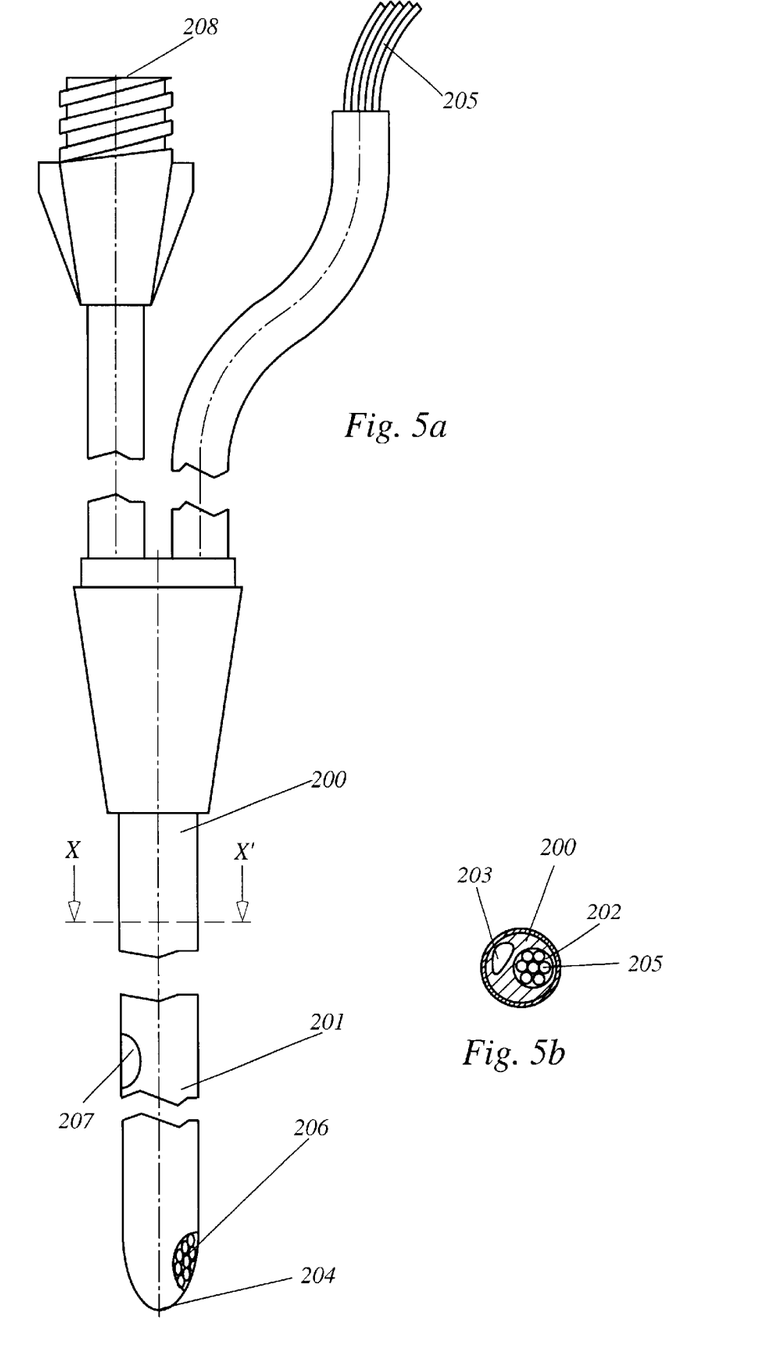
FIG. 5a schematically shows another preferred embodiment of a central venous catheter assembly according to the present invention.
FIG. 5b schematically shows a cross-sectional view of the extended portion of the catheter assembly of FIG. 5a with plane of section X–X'.

FIGS. 5a–b illustrate another central venous catheter assembly embodying the present invention with FIG. 5b showing a cross-sectional view with plane of section indicated X–X' in FIG. 5a. The catheter assembly includes an elongated catheter body 200 including an intravascular catheter portion 201 adapted to be inserted, distal end 204 first, in a patient's vena cava superior. The intravascular catheter portion 201 has a length of approximately 15 cm and is capable of flexing during insertion but has sufficient rigidity to allow unproblematic handling and to prevent a first lumen 202 and a second lumen 203 to collapse. A fiberoptic bundle 205 fitting into the first lumen 202 may either be permanently secured to the catheter body 200 or inserted into the first lumen 202 after the intravascular catheter portion 201 has been inserted into the vena cava superior. The fiberoptic bundle 205 is used to conduct light pulses from a source (not shown) to the outlet 206 of the first lumen 202 close to the distal end 204 in order to emit heat pulses in the immediate proximity of the distal end 204, thus transmitting energy from the source to the patient's blood stream once the intravascular catheter portion 201 has been inserted into the vena cava superior. The power transferred by emitting each heat pulse represents a respective input signal for modified transpulmonary thermodilution measurements in the context of hemodynamic monitoring. Additionally, a portion of the fibers of the fiberoptic bundle 205 can be used to transmit reflected light from the blood back to a detector (not shown). If the light source is modulated with different wavelengths, i.e one wavelength that is substantially absorbed by the blood and one reference wavelength that is mostly reflected, the information of the reflected radiation can be used to control the energy which is transferred to the patients blood stream. If, furthermore, the wavelengths are chosen to be within the range of wavelenghts commonly used in spectrometric blood oxygen saturation measurements, the central venous blood oxygen saturation can be determined by the reflected intensities for the various wavelengths. The second lumen 203, which can be accessed at its proximal end 208, can be used for other purposes such as blood sampling. The outlet 206 of the first lumen 202 is closer to the distal end 204 of the catheter assembly than the outlet 207 of the second lumen 203. The catheter assembly may comprise additional lumina for other purposes.

What is claimed is:

1. Apparatus for hemodynamic monitoring, said apparatus comprising
    (a) a central venous catheter assembly having a proximal end and a distal end, said central venous catheter assembly comprising at least one lumen and heating means in the immediate proximity of said distal end adapted to emit heat pulses for introducing travelling temperature deviations to a patient's blood circulation,
    (b) means for determining the power transferred by the heating means as a function of time, the power transferred during emission of each heat pulse thereby representing an input signal corresponding to the respective heat pulse, (c) an arterial catheter assembly comprising temperature sensing means for measuring the local blood temperature in an artery of said patient as a function of time, thus determining for each said input signal a corresponding system response, and (d) computing means having implemented thereon executable operations for determining a reference cardiac output value of said patient from at least one said input signal and said respective corresponding system response.

2. Apparatus as claimed in claim 1 wherein said computing means has additionally implemented thereon executable operations for determining at least one parameter of the group of global end-diastolic volume, intrathoric blood volume and extravascular thermovolume of said patient from at least one said input signal and said respective corresponding system response.

3. Apparatus as claimed in claim 1, wherein said central venous catheter assembly is adapted to emit said heat pulses at at least one predefined pattern of a group of patterns including sinusoidal waves and step functions with predefined amplitudes and durations.

4. Apparatus as claimed in claim 1, wherein said central venous catheter assembly is adapted to emit said heat pulses at random.

5. Apparatus as claimed in claim 1, wherein said heating means comprises one of the group of an electrically heatable filament and a heating coil.

6. Apparatus as claimed in claim 1, wherein said heating means comprises means for emitting electromagnetic radiation comprising a fiberoptic bundle which is insertable into said lumen of said catheter assembly.

7. Apparatus as claimed in claim 1, wherein said heating means comprises means for emitting electromagnetic radiation comprising a fiberoptic bundle which is mounted into said lumen of said catheter assembly.

8. Apparatus as claimed in any of claims 6 or 7, wherein said electromagnetic radiation is modulated electromagnetic radiation at different wavelenghts, and said fiberoptic bundle comprises at least one fiber adapted to collect reflected radiation at said different wavelengths and said computing means additionally has implemented instructions thereon to determine from said reflected radiation the central venous oxygen saturation.

9. Apparatus as claimed in claim 1, wherein said central venous catheter assembly comprises means for measuring the central venous blood pressure.

10. Apparatus as claimed in claim 1, wherein determining said reference cardiac output value includes statistic evaluation of a plurality of said input signals and respective corresponding system responses.

11. Apparatus as claimed in claim 1, wherein said arterial catheter assembly additionally comprises pressure sensing means for measuring said patient's arterial blood pressure AP(t) as a function of time, thus creating an arterial blood pressure curve, and said computing means has implemented thereon executable operations for repeatedly determining hemodynamic parameters from said arterial blood pressure curve by pulse contour analysis using said reference cardiac output value.

12. Apparatus as claimed in claim 11, wherein said hemodynamic parameters comprise at least one parameter from the group pulse contour cardiac output PCCO, stroke volume SV and stroke volume variation SVV.

13. Apparatus as claimed in claim 11, wherein said computing means additionally has implemented thereon instructions to recalculate said hemodynamic parameters obtained from said arterial blood pressure curve and said reference cardiac output value after determining said reference cardiac output value.

14. Apparatus as claimed in claim 1 or claim 11, wherein said central venous catheter assembly comprises an additional lumen for thermal indicator injection for performing transpulmonary thermodilution measurements in order to obtain an initial reference cardiac output value for initial calibration.

15. Apparatus for hemodynamic monitoring, said apparatus comprising (a) a central venous catheter assembly having a proximal end and a distal end, said central venous catheter assembly comprising at least one lumen and heating means in the immediate proximity of said distal end adapted to emit heat pulses for, introducing travelling temperature deviations to a patient's blood circulation, (b) means for determining the power transferred by the heating means as a function of time, the power transferred during emission of each heat pulse thereby representing an input signal corresponding to the respective heat pulse, (c) an arterial catheter assembly comprising temperature sensing means for measuring the local blood temperature in an artery of said patient as a function of time, thus determining for each said input signal a corresponding system response, and pressure sensing means for measuring said patient's arterial blood pressure AP(t) as a function of time, thus creating an arterial blood pressure curve, and (d) computing means having implemented thereon executable operations for determining a reference cardiac output value of said patient from at least one said input signal and said respective corresponding system response and for repeatedly determining hemodynamic parameters from said arterial blood pressure curve by pulse contour analysis using said reference cardiac output value.

16. Central venous catheter assembly for hemodynamic monitoring, said central venous catheter assembly having a proximal and a distal end and comprising:

(a) at least one lumen;

(b) heating means in the immediate proximity of said distal end; and (c) wherein said catheter assembly does not include a temperature sensing means for measuring the local blood temperature.

17. Central venous catheter assembly as claimed in claim 16, wherein said heating means comprises one of the group of an electrically heatable filament or heating coil.

18. Central venous catheter assembly as claimed in claim 16 wherein said heating means are means for emitting electromagnetic radiation.

19. Central venous catheter assembly as claimed in claim 18, wherein said means for emitting electromagnetic radiation comprises a fiberoptic bundle which is insertable into one of said lumina of said catheter assembly.

20. Central venous catheter assembly as claimed in claim 18,
wherein said means for emitting electromagnetic radiation comprises a fiberoptic bundle which is mounted into one of said lumina of said catheter assembly.

21. Central venous catheter assembly as claimed in any of claims 19–20,
wherein said electromagnetic radiation is modulated electromagnetic radiation at different wavelenghts and said fiberoptic bundle comprises at least one fiber adapted to collect reflected radiation at said different wavelengths.

22. Central venous catheter assembly as claimed in claim 19,
wherein said lumen into which said fiberoptic bundle is insertable has an opening closer to the distal end of said catheter assembly than all the openings of all the other lumina of said catheter assembly.

23. Central venous catheter assembly as claimed in claim 20,
wherein said lumen into which said fiberoptic bundle is mounted has an opening closer to the distal end of said catheter assembly than all the openings of all the other lumina of said catheter assembly.

24. Central venous catheter assembly as claimed in claim 16,
wherein the distance between said heating means and said distal end is less than 20 mm.

25. Central venous catheter assembly as claimed in claim 16,
wherein said central venous catheter assembly comprises means for measuring the central venous blood pressure.

26. Central venous catheter assembly as claimed in claim 16,
wherein said central venous catheter assembly comprises an additional lumen for thermal indicator injection for performing transpulmonary thermodilution measurements.

27. Hemodynamic monitoring method comprising the steps of
(a) providing a central venous catheter assembly having a proximal end and a distal end, said central venous catheter assembly comprising at least one lumen and heating means in the immediate proximity of said distal end
(b) emitting heat pulses through said heating means for introducing travelling temperature deviations to a patient's blood circulation,
(c) determining the power transferred by the heating means as a function of time, the power transferred during emission of each heat pulse thereby representing an input signal corresponding to the respective heat pulse,
(d) providing an arterial catheter assembly comprising temperature sensing means and pressure sensing means
(e) measuring through said temperature sensing means the local blood temperature in an artery of said patient as a function of time, thus determining for each said input signals a corresponding system response,
(f) measuring through said pressure sensing means said patient's arterial blood pressure AP(t) as a function of time, thus creating an arterial blood pressure curve
(g) determining a reference cardiac output value of said patient from at least one said input signal and said respective corresponding system response.

28. Hemodynamic monitoring method comprising the steps of
(a) providing a central venous catheter assembly having a proximal end and a distal end, said central venous catheter assembly comprising at least one lumen and heating means in the immediate proximity of said distal end
(b) emitting heat pulses through said heating means for introducing travelling temperature deviations to a patient's blood circulation,
(c) determining the power transferred by the heating means as a function of time, the power transferred during emission of each heat pulse thereby representing an input signal corresponding to the respective heat pulse,
(d) providing an arterial catheter assembly comprising temperature sensing means and pressure sensing means
(e) measuring through said temperature sensing means the local blood temperature in an artery of said patient as a function of time, thus determining for each said input signals a corresponding system response,
(f) measuring through said pressure sensing means said patient's arterial blood pressure AP(t) as a function of time, thus creating an arterial blood pressure curve
(g) determining a reference cardiac output value of said patient from at least one said input signal and said respective corresponding system response, and
(h) determining repeatedly hemodynamic parameters from said arterial blood pressure curve by pulse contour analysis using said reference cardiac output value.

29. Hemodynamic monitoring method as claimed in claim 28,
wherein said heat pulses are emitted at random or at a predefined pattern of a group of patterns including sinusoidal waves and step functions with predefined amplitudes and durations.

30. Hemodynamic monitoring method as claimed in claim 28,
wherein said heat pulses are emitted at random.

31. Hemodynamic monitoring method as claimed in claim 28,
wherein determining said hemodynamic parameters comprises the steps of
(1) calculating a mean arterial blood pressure MAP from said arterial blood pressure AP(t) measured as a function of time,
(2) calculating a systemic vascular resistance SVR of said patien according to the formula $$SVR = (MAP - CVP)/CO_{ref}$$

with CVP being an arbitrary central venous pressure which is measured, ascertained or estimated, and $CO_{ref}$ being said reference cardiac output,
(3) calculating the driving blood pressure p(t) according to the formula $$p(t) = AP(t) - CVP$$

(4) calculating at least the first derivative of the driving blood pressure with respect to time ṗ(t)=dp/dt, and
(5) determining said hemodynamic parameters from at least p(t), ṗ(t) and SVR according to a non-linear model.

32. Hemodynamic monitoring method as claimed in claim 31, wherein said step of determining said hemodynamic parameters from at least p(t), ṗ(t) and SVR according to a non-linear model includes determining a blood flow q(t) on the basis of said driving blood pressure p(t) and the first derivative with respect to time ṗ(t), and calculating the compliance function according to $$C(p) = \frac{q(t) - p(t)/SVR}{\dot{p}(t) - Z(p) \cdot (\dot{q}(t) - \dot{p}(t)/SVR)}$$

for arbitrary impedance functions Z(p) and arbitrary times t in such a way that $$q(t) = \frac{p(t)}{SVR} + C(p)\left[\dot{p}(t) - Z(p) \cdot (\dot{q}(t) - \frac{\dot{p}(t)}{SVR})\right]$$

is optimally satisfied.

33. Hemodynamic monitoring method as claimed in claim 28, wherein said hemodynamic parameters comprise at least one parameter from the group pulse contour cardiac output PCCO, stroke volume SV and stroke volume variation SVV.

34. Computer program for hemodynamic monitoring encoded on a computer-readable medium, said computer program comprising instructions executable by a computer system to repeatedly perform the steps of
    (a) determining a reference cardiac output value by statistic evaluation of a plurality of input signals and respective corresponding system responses,
        said input signals representing the power transferred during emission of a plurality of heat pulses as a function of time,
        said heat pulses introducing traveling temperature deviations to a patient's blood circulation,
        said corresponding system responses being determined by measuring the local blood temperature in an artery of said patient as a function of time, and
    (b) determining hemodynamic parameters from an arterial blood pressure curve by pulse contour analysis using said reference cardiac output value,
        said arterial blood pressure curve being determined by measuring the arterial blood pressure in an artery of said patient as a function of time.

35. Computer program encoded on a computer-readable medium as claimed in claim 34,
    wherein determining said hemodynamic parameters comprises the steps of
    (1) calculating a mean arterial blood pressure MAP from said arterial blood pressure AP(t) measured as a function of time,
    (2) calculating a systematic vascular resistance SVR of said patient according to the formula $$SVR=(MAP-CVP)/CO_{ref}$$

with CVP being an arbitrary central venous pressure which is measured, ascertained or estimated, and $CO_{ref}$ being said reference cardiac output,
    (3) calculating the driving blood pressure p(t) according to the formula $$p(t)=AP(t)-CVP$$

(4) calculating at least the first derivative of the driving blood pressure with respect to time ṗ(t)=dp/dt, and
    (5) determining said hemodynamic parameters from at least p(t), ṗ(t) and SVR according to a non-linear model.

36. Computer program encoded on a computer-readable mediuum as claimed in claim 35,
    wherein said step of determining said hemodynamic parameters from at least p(t), ṗ(t) and SVR according to a non-linear model includes determining a blood flow q(t) on the basis of said driving blood pressure p(t) and the first derivative with respect to time ṗ(t),
    and calculating the compliance function according to $$C(p) = \frac{q(t) - p(t)/SVR}{\dot{p}(t) - Z(p) \cdot (\dot{q}(t) - \dot{p}(t)/SVR)}$$

for arbitrary impedance functions Z(p) and arbitrary times t in such a way that $$q(t) = \frac{p(t)}{SVR} + C(p)\left[\dot{p}(t) - Z(p) \cdot (\dot{q}(t) - \frac{\dot{p}(t)}{SVR})\right]$$

is optimally satisfied.

37. Computer program encoded on a computer-readable medium as claimed in claim 34,
    wherein said hemodynamic parameters comprise at least one parameter from the group pulse contour cardiac output PCCO, stroke volume SV and stroke volume variation SVV.

* * * * *